United States Patent [19]

Ohno et al.

[11] 4,176,135
[45] Nov. 27, 1979

[54] PROCESS FOR PREPARING HYDRAZODICARBONAMIDE

[75] Inventors: Shigeaki Ohno, Naruto; Toshiyuki Kazuta, Tokushima; Takeshi Iwata, Naruto, all of Japan

[73] Assignee: Otsuka Kagaku Yakuhin Kabushiki Kaisha, Osaka, Japan

[21] Appl. No.: 871,410

[22] Filed: Jan. 23, 1978

[30] Foreign Application Priority Data

Mar. 24, 1977 [JP] Japan .................................. 52-33111

[51] Int. Cl.$^2$ ............................................. C07C 133/02
[52] U.S. Cl. ...................................... 260/554; 546/244; 260/347.7; 546/186; 546/214; 542/417
[58] Field of Search ............... 260/554, 347.7, 293.87

[56] References Cited

U.S. PATENT DOCUMENTS

| | | | |
|---|---|---|---|
| 2,692,281 | 10/1954 | Newby et al. | 260/554 |
| 3,153,089 | 10/1964 | Ameen | 260/554 X |
| 3,969,466 | 7/1976 | Brown et al. | 260/554 |
| 4,049,712 | 9/1977 | Schirmann et al. | 260/554 |

FOREIGN PATENT DOCUMENTS 46-35251 10/1971 Japan ........................................ 260/554

*Primary Examiner*—Thomas A. Waltz
*Attorney, Agent, or Firm*—Toren, McGeady and Stanger

[57] ABSTRACT

Hydrazodicarbonamide is prepared by reacting a compound represented by

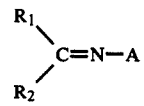

with urea while the former is being continuously or intermittently introduced into the reaction system and while the carbonyl compound and ammonia produced as by-products are being withdrawn from the system.

13 Claims, No Drawings

PROCESS FOR PREPARING HYDRAZODICARBONAMIDE

This invention relates to a novel process for preparing hydrazodicarbonamide.

Hydrazodicarbonamide ($H_2NCONHNHCONH_2$) is useful as an intermediate in the preparation of azodicarbonamide ($H_2NCON=NCONH_2$) which is useful as an organic blowing agent for rubbers and resins.

Various processes have heretofore been developed for the preparation of hydrazodicarbonamide. The compound can be prepared for example by:

(1) Reacting hydrazine hydrate or a salt thereof with urea with heating in the presence of a non-oxidizing mineral acid such as sulfuric acid, phosphoric acid or hydrochloric acid.

(2) Reacting hydrazine hydrate or a salt thereof with urea with heating in an aqueous alkaline solution while removing the resulting ammonia from the system (Japanese Published Unexamined Patent Application No. 11719/1976).

(3) Reacting a ketazine with urea with heating in the presence of a non-oxidizing mineral acid (British Pat. No. 1371119).

(4) Reacting a ketazine with urea with heating in an aqueous alkaline solution while recovering ammonia, ketone and unhydrolyzed ketazine by fractional distillation (U.S. Pat. No. 3,969,466).

However, these processes have their inherent drawbacks. The process (1) requires a non-oxidizing mineral acid in an amount at least equivalent to the ammonia produced and necessitates a sophisticated treatment for the disposal of the effluent from the process. Although the process (2) does not have such drawbacks, the production cost is not as low as is satisfactory. The process (3) in which hydrazodicarbonamide is produced from a ketazine via hydrazine hydrate also involves the same drawbacks as the process (1). Whereas the process (4) does not require the use of any mineral acid, the process is not fully advantageous over other processes because of low yields of hydrazodicarbonamide, which permit a side reaction such as condensation of ketone, leading to reduced ketone recovery efficiencies. The loss of ketone as well as of expensive hydrazine component inevitably renders the product costly.

An object of this invention is to provide a process for preparing hydrazodicarbonamide in exceedingly high yields.

Another object of this invention is to provide a process for preparing hydrazodicarbonamide without using any mineral acid and with the advantage that the effluent from the process is easy to treat.

Another object of this invention is to provide a process for preparing hydrazodicarbonamide which permits efficient recovery of carbonyl compound and which is therefore very advantageous in production cost.

These and other objects of this invention will become apparent from the following description.

The present invention provides a process for preparing hydrazodicarbonamide by reacting a compound represented by the formula

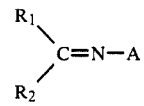

(1)

wherein $R_1$ is hydrogen atom or alkyl having from 1 to 4 carbon atoms, $R_2$ is alkyl having from 1 to 4 carbon atoms, cycloalkyl having from 4 to 8 carbon atoms or aryl having from 6 to 10 carbon atoms, $R_1$ and $R_2$, when taken together with the carbon atom to which they are attached, may form an aliphatic ring or heterocyclic ring, and A is $NH_2—$ or

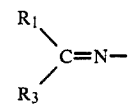

wherein $R_1$ is as defined above, $R_3$ is alkyl having from 1 to 4 carbon atoms, cycloalkyl having from 4 to 8 carbon atoms or aryl having from 6 to 10 carbon atoms, and $R_1$ and $R_3$, when taken together with the carbon atom to which they are attached, may form an aliphatic ring or heterocyclic ring, with urea in an aqueous medium with heating, the process being characterized in that the compound of the formula (1) is continuously or intermittently introduced into the reaction system while the carbonyl compound and ammonia produced are being withdrawn from the reaction system.

In the preparation of hydrazodicarbonamide, no attempts have heretofore been made to continuously or intermittently introduce the starting compound into the reaction system. Thus this invention is an entirely novel process which gives the desired product, i.e. hydrazodicarbonamide, in extremely high yields. Moreover the present process, in which the ammonia produced as a by-product is withdrawn from the reaction system, affords the desired compound merely with use of a simple apparatus, through a simple procedure and free of pollution problems, without the use of a mineral acid which would eventually entail the necessity of sophisticated treatment. Additionally the present process does not require much heat energy, permits efficient recovery of carbonyl compound and is accordingly economically advantageous.

Examples of useful compounds represented by the formula (1) are ketazines or aldazines of the formula

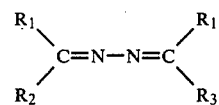

(2)

and hydrazones of the formula

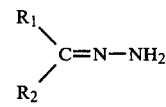

(3)

In these formulae, $R_1$ is hydrogen atom or alkyl having from 1 to 4 carbon atoms, $R_2$ ($R_3$) is alkyl having from 1 to 4 carbon atoms, cycloalkyl having from 4 to 8 carbon atoms or aryl having from 6 to 10, and $R_1$ and $R_2$ ($R_3$), when taken together with the carbon atom to which they are attached, may form an aliphatic ring or heterocyclic ring. Examples of useful alkyl groups are methyl, ethyl, propyl, butyl and the like. Examples of suitable cycloalkyl groups are cyclobutyl, cyclopentyl, cyclohexyl, cycloheptyl, cyclooctyl, 2-methylcyclohexyl and the like. Examples of suitable aryl groups are phenyl, tolyl, xylyl and the like. Examples of aliphatic rings are cyclopentylidene, cyclohexylidene and the like. Examples of heterocyclic rings are

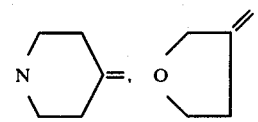

and the like. More specific examples of ketazines and aldazines of the formula (2) are dimethylketazine, methylethylketazine, methylisopropylketazine, diethylketazine, methylisobutylketazine, dibutylketazine, cyclohexylmethylketazine, cyclobutylketazine, cyclopentylketazine, cyclohexylketazine, cycloheptylketazine, cyclooctylketazine, 2-methylcyclohexylketazine, acetoaldazine, propioaldazine, cyclopentylaldazine, cyclohexylaldazine, benzaldazine and the like.

More specific examples of hydrazones of the formula (3) are acetone hydrazone, methyl ethyl ketone hydrazone, cyclohexyl ketone hydrazone, acetaldehyde hydrazone, propionaldehyde hydrazone, cyclohexylaldehyde hydrazone, benzaldehyde hydrazone and the like. Among the compounds represented by the formulae (2) and (3), preferable are those in which $R_1$, $R_2$ and $R_3$ are each alkyl having from 1 to 4 carbon atoms and also those in which $R_2$ and $R_3$ are the same. According to this invention, the compounds of the formulae (2) and (3) can be used singly or in admixture, as they are or as dissolved in water or in an aqueous medium.

The other starting material of this invention, namely urea, can be used in the form of a solid or as dissolved in water or in an aqueous medium. The amount of urea to be used is not particularly limited; it can be used in large excess. Usually about 2 to about 10 moles, preferably about 3 to about 6 moles, of urea is used per mole of the compound of the formula (1). The excess urea not participating in the reaction is recovered as contained in the mother liquor and reusable for the reaction.

Examples of aqueous media useful in this invention are water and mixtures of water and solvents which are miscible with water. Examples of such solvents are methanol, ethanol and like alcohols, dimethylformamide, etc. The aqueous media may contain a surfactant. Also usable as such media are solvents useful for the preparation or recovery of the compounds of the formula (1). Examples are aqueous solutions containing heptanol, amyl alcohol, etc.

The effects of this invention can be achieved with improved results when the reaction is conducted in the presence of a soluble salt. Soluble salts useful in this invention are various metal salts and ammonia salts having no oxidizing properties but possessing a solubility of at least about 0.1 wt. % in the aqueous medium. Examples of useful salts are metal salts of mineral acids, ammonium salts of mineral acids, metal salts of organic acids, ammonium salts of organic acids, etc. Examples of more specific salts are sodium sulfate, ammonium chloride, ammonium sulfate, sodium acetate and the like. These soluble salts are used singly or in admixture. Usually about 0.01 to about 10 moles, preferably about 0.1 to about 3 moles, of such soluble salts are used per mole of the compound of the formula (1).

According to this invention, the compound of the formula (1) is continuously or intermittently introduced, as it is or in the form of a solution, into the reaction system.

The introduction of the compound of the formula (1) to the reaction system, when effected in the above-mentioned manner, effectively inhibit side reaction, giving hydrazodicarbonamide in high yields.

The reaction temperature in this invention, which is suitably determined in accordance with the amount of urea used, the amount of soluble salt used, the progress of the reaction and the like, is usually about 60° to about 140° C., preferably about 99° to about 125° C. It is preferable to conduct the reaction with the system maintained at a pH of 7 to 11. The reaction time, which is not particularly limited, is usually about 4 to about 8 hours, whereby satisfactory results can be achieved. Preferably the reaction is carried out at increased pressure. This serves to elevate the temperature of the reaction system and leads to a higher reaction efficiency. The reaction of this invention is effected while the carbonyl compound and ammonia resulting from the reaction as by-products are being withdrawn from the system. The reaction forms ketone as the carbonyl compound except when $R_1$ of the formula (1) representing the starting material is hydrogen, in which case the carbonyl by-product is aldehyde.

The removal of the carbonyl compound and ammonia from the reaction system expedites the reaction, inhibiting the possible side reaction and affording the desired product in good yields. The carbonyl compound and ammonia recovered are reusable for the synthesis of hydrazine as well as for the preparation of ketazines, aldazines and hydrazones. The process of this invention assures the recovery of the regenerated carbonyl compound with high effiencies without permitting the reaction of the by-product.

For a better understanding of this invention, Examples and Comparison Examples are given below.

EXAMPLE 1

A 530 g quantity of 62.3 wt. % aqueous urea solution (containing 5.5 moles of urea) is placed into one-liter four-necked flask equipped with a stirrer, thermometer, heating bath and fractionating column of sufficient capacity, and 132 g (1.0 mole) of ammonium sulfate is added to the solution.

The mixture is heated with stirring. On commencement of boiling, 182.1 g of 61.5 wt. % of aqueous solution of dimethylketazine is continuously added dropwise to the mixture over a period of 4 hours through a dropping funnel attached to the flask. The resulting mixture is thereafter allowed to react for a further 2 hours while being maintained at a temperature of 100° to 105° C. The ketone and ammonia produced during the reaction are withdrawn from the reaction system. After the reaction, 100 ml of water is added to the mixture for dilution, and the mixture is cooled to 60° C., giving white crystals. The crystals are filtered off, thoroughly washed with water and dried at 110° C. The crystals weight 113.1 g, yield 95.8% based on the ketazine used. A 110.5 g quantity of acetone is recovered. The recovery efficiency is 94.5% in view of the excess acetone (1.5 g) contained in the ketazine used.

EXAMPLE 2

In the same manner as in Example 1 except that ammonium sulfate is not used, 107.3 g of hydrazodicarbonamide (HDCA) is obtained, yield 90.9%. Ketone recovery efficiency: 90.1%.

COMPARISON EXAMPLE 1

A 530 g quantity of 62.3 wt. % aqueous urea solution and 182.1 g of 61.5 wt. % aqueous solution of dimethylketazine are placed into the same one-liter four-necked flask as used in Example 1. The mixture is reacted with stirring for 8 hours while being maintained at a temperature of 100° to 105° C. by heating. The reaction mixture is thereafter treated in the same manner as in Example 1, giving 96.6 g of HDCA, yield 81.8%. Ketone recovery efficiency: 80.2%.

Table 1 shows the results achieved in Examples 1 and 2 and Comparison Example 1.

Table 1

|  | HDCA yield (%) | Ketone recovery efficiency (%) |
|---|---|---|
| Example 1 | 95.8 | 94.5 |
| Example 2 | 90.9 | 90.1 |
| Comp. Ex. 1 | 81.8 | 80.2 |

EXAMPLE 3

HDCA is prepared in the same manner as in Example 1 except that dimethylketazine is replaced by an equal amount in mole of methylethylketazine.

EXAMPLE 4

HDCA is prepared in the same manner as in Example 2 except that dimethylketazine is replaced by an equal amount in mole of methylethylketazine.

COMPARISON EXAMPLE 2

HDCA is prepared in the same manner as in Comparison Example 1 except that in place of dimethylketazine an equal amount in mole of methylethylketazine is used.

Table 2 shows the results achieved in Examples 3 and 4 Comparison Example 2.

Table 2

|  | HDCA yield (%) | Ketone recovery efficiency (%) |
|---|---|---|
| Example 3 | 98.1 | 97.5 |
| Example 4 | 96.8 | 96.0 |
| Comp. Ex. 2 | 90.5 | 90.1 |

EXAMPLE 5

A 530 g quantity of 62.3 wt. % aqueous urea solution and 322.2 g of sodium sulfate decahydrate are placed into the same four-necked flask as used in Example 1. The mixture is heated with stirring. On commencement of boiling, 192 g of cyclohexylketazine is added dropwise to the mixture over a period of 9 hours through a dropping funnel attached to the flask. A 20 g portion of the ketazine is added first and a 10 g portion thereof is therefter added every 30 minutes. The resulting mixture is heated for a further 4 hours. The reaction between the cyclohexylketazine and urea slowly gives a fraction of free cyclohexanone with water distilled off from the system, so that the reaction is carried out with addition of water to keep the initial liquid level. The reaction affords 108 g of white crystals, yield of HDCA 91.5%. Ketone recovery efficiency: 89%.

EXAMPLE 6

HDCA is prepared in the same manner as in Example 5 except that 192 g of cyclohexylketazine is added dropwise to the mixture continuously over a period of 9 hours. The reaction affords 109 g of white crystals, yield 92.4%.

EXAMPLE 7

HDCA is prepared in the same manner as in Example 5 except that 66 g of ammonium sulfate is used in place of 322.2 g of sodium sulfate decahydrate and 164 g of cyclopentylketazine is added dropwise to the mixture continuously over a period of 5.5 hours. The reaction affords 101 g of white crystals, yields 85.6%.

EXAMPLE 8

A solution of 180 g of urea in 200 ml of water and 66 g of ammonium sulfate are placed into the same four-necked flask as used in Example 1. The mixture is heated with stirring. On commencement of boiling, a dispersion of 104 g of benzaldazine in 100 ml of water is added dropwise to the mixture at a rate of 25 g/hour. With the progress of the reaction, free benzaldehyde is distilled off from the system through the fractionating column. After the completion of dropwise addition of the dispersion, the mixture is reacted for a further 7 hours, giving 53.5 g of white crystals, yield 90.5%. Aldehyde recovery efficiency: 87%.

What is claimed is:

1. A process for preparing hydrazodicarbonamide by reacting a compound represented by the formula

wherein
$R_1$ is hydrogen atom or alkyl having from 1 to 4 carbon atoms;
$R_2$ is alkyl having from 1 to 4 carbon atoms, cycloalkyl having from 4 to 8 carbon atoms or aryl having from 6 to 10 carbon atoms;
$R_1$ and $R_2$, when taken together with the carbon atom to which they are attached, form an aliphatic ring or heterocyclic ring; and
A is $NH_2$— or

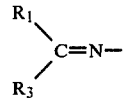

wherein
$R_1$ is as defined above,
$R_3$ is alkyl having from 1 to 4 carbon atoms, cycloalkyl having from 4 to 8 carbon atoms or aryl having from 6 to 10 carbon atoms, and $R_1$ and $R_3$, when taken together with the carbon atom to which they are attached, form an aliphatic ring or heterocyclic ring,
wherein urea in an aqueous medium with heating in the absence of any added mineral acid and in the presence of a salt selected from the group consisting of metal salts of mineral acid, ammonium salts of mineral acid, metal salts of organic acid and ammonium salts of organic acid, having a solubility of at least about 0.1 wt. % in the aqueous medium and wherein the compound of formula (1) is continuously or intermittently introduced into the reaction system while the carbonyl compound and ammonia produced are being withdrawn from the reaction system.

2. A process as defined in claim 1 wherein $R_1$, $R_2$ and $R_3$ in the formula (1) are each alkyl having from 1 to 4 carbon atoms.

3. A process as defined in claim 1 wherein $R_2$ and $R_3$ in the formula (1) are the same.

4. A process as defined in claim 1 wherein $R_2$ in the formula (1) is cycloalkyl.

5. A process as defined in claim 1 wherein $R_1$ and $R_2$ or $R_1$ and $R_3$ in the formula (1) taken together with the carbon atom to which they are attached form an aliphatic ring.

6. A process as defined in claim 1 wherein A in the formula (1) is

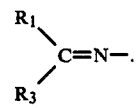

7. A process as defined in claim 1 wherein A in the formula (1) is $NH_2$—.

8. A process as defined in claim 1 wherein the aqueous medium is water or a mixture of water and a solvent miscible with water.

9. A process as defined in claim 1 wherein the compound of the formula (1) is continuously introduced into the reaction system.

10. A process as defined in claim 1 wherein the compound of the formula (1) is intermittently introduced into the reaction system.

11. A process as defined in claim 1 wherein the soluble salt is sodium sulfate, ammonium chloride, ammonium sulfate or sodium acetate.

12. A process as defined in claim 1 wherein the reaction is conducted with the system maintained at a pH of 7 to 11.

13. A process as defined in claim 1 wherein the reaction is conducted with application of pressure.

* * * * *